(12) United States Patent
Ballinger, Jr.

(10) Patent No.: US 6,328,986 B1
(45) Date of Patent: Dec. 11, 2001

(54) METHOD OF DETERRING BIRDS FROM PLANT AND STRUCTURAL SURFACES

(75) Inventor: Kenneth E. Ballinger, Jr., Kennett Square, PA (US)

(73) Assignee: Arkion Life Sciences, Wilmington, DE (US)

( * ) Notice: Subject to any disclaimer, the term of this patent is extended or adjusted under 35 U.S.C. 154(b) by 0 days.

(21) Appl. No.: 09/549,637

(22) Filed: Apr. 14, 2000

Related U.S. Application Data

(63) Continuation-in-part of application No. 08/812,869, filed on Mar. 6, 1997, now abandoned, and a continuation-in-part of application No. 08/918,800, filed on Aug. 26, 1997, now Pat. No. 5,885,604, which is a continuation-in-part of application No. 08/633,878, filed on Apr. 10, 1996, now abandoned, which is a continuation-in-part of application No. 08/919,294, filed on Aug. 28, 1997, now abandoned, which is a continuation-in-part of application No. 09/060,442, filed on Apr. 15, 1998, now abandoned.

(51) Int. Cl.$^7$ .................................................. A01N 25/12

(52) U.S. Cl. .................. 424/405; 424/406; 424/409; 424/421; 514/680; 514/690; 514/691; 514/920

(58) Field of Search ...................... 514/918, 920, 514/679–682, 688, 690, 691; 424/405–407, 409–421

(56) References Cited

U.S. PATENT DOCUMENTS

| | | | |
|---|---|---|---|
| 3,663,253 | * | 5/1972 | Stone .................................. 706/204 |
| 5,549,902 | * | 8/1996 | Preiser et al. .................... 424/405 |
| 5,672,352 | * | 9/1997 | Clark et al. ........................ 424/405 |

OTHER PUBLICATIONS

Merck Index Anthraquinone, 1968.*

* cited by examiner

Primary Examiner—Neil S. Levy
(74) Attorney, Agent, or Firm—Basil S. Krikelis

(57) ABSTRACT

A method for deterring birds from perching, roosting or loafing on plant and structural surfaces by applying to the surfaces a non-toxic composition. The non-toxic composition is one that triggers a physiological aversion mechanism in birds by a visual cue and a post-ingestinal response.

7 Claims, 3 Drawing Sheets

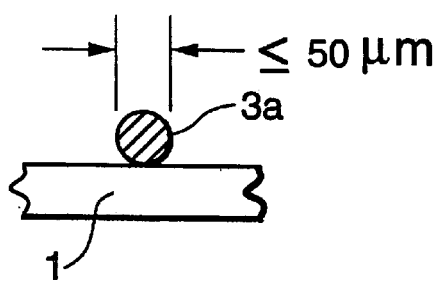
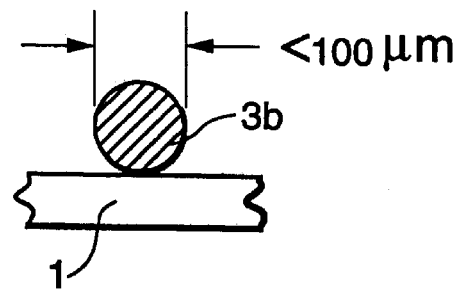
Fig. 1a                Fig. 1b
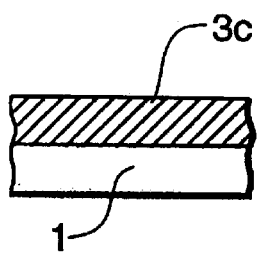
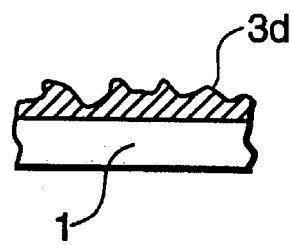
Fig. 1c                Fig. 1d
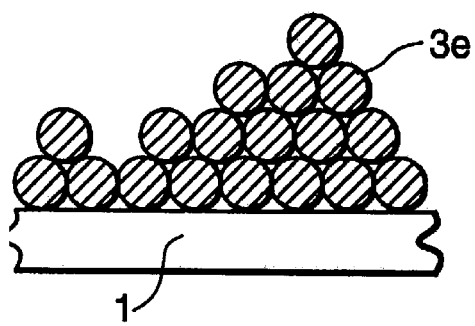
Fig. 1e

METHOD OF DETERRING BIRDS FROM PLANT AND STRUCTURAL SURFACES

CROSS-REFERENCE TO RELATED APPLICATIONS

This application is a continuation-in-part of U.S. patent applications Ser. No. 08/812,869, now abandoned, filed Mar. 6, 1997; Ser. No. 08/918,800, U.S. Pat. No. 5,885,604 filed Aug. 26, 1997, which was a continuation-in-part of Ser. No. 08/633,878, filed Apr. 10, 1996, and now abandoned; and Ser. No. 08/919,294, filed Aug. 28, 1997; and now abandoned; Ser. No. 09/060,442, filed Apr. 15, 1998, abandoned.

FIELD OF THE INVENTION

The invention is directed to a method for deterring birds from roosting, perching or loafing on plant and solid or structural surfaces.

BACKGROUND OF THE INVENTION

The co-existence of humans and wild birds has always been an important relationship for both species. For humans, this relationship has been a pleasant one esthetically and a useful one ecologically. In the former case, the sights and sounds of birds are universally enjoyed by people of all ages. In the latter case, the role of birds in the ecological chain vis-à-vis birds, carrion and other species is essential. It is, of course, essential that both relationships be preserved.

Notwithstanding the beneficial and pleasant aspects of the interface between wild birds and humans, the propensity of birds to alight on, occupy and damage solid surfaces associated with or near human activity frequently becomes a source of conflict.

A source of conflict between birds and humans is associated with areas of grassy turf on or around which there is substantial human activity, for example, birds can frequently become a nuisance and cause substantial damage to pedestrian traveled areas, such as golf courses, cemeteries and campuses. These areas, which require substantial upkeep, especially golf courses, suffer much due to birds nesting and gathering on them. For example, they can become a distraction because of the noise a flock can generate. Birds also become a nuisance because of the fecal deposits they leave. Fecal deposits are not only a nuisance due to the mess they cause, but also a public health concern due to the parasites and/or the disease that live in and spread from the droppings.

Another area of major concern is roosting birds near the end of runways at commercial and military airports. Roosting birds can cause "bird strikes" whereby many birds take flight near aircraft that are taking off or landing, which result in birds colliding with the aircraft or being sucked into the engines. This causes damage to the aircraft by damaging the canopy or the wings and engines. In some instances, birds have caused aircraft engines to fail completely and the plane to crash, which results in complete loss of the aircraft and in some instances has resulted in loss of human life. The Federal Aviation Administration receives as many as 2,000 reports of bird strikes each year. Major airlines report they sustain over $12 million of damage per year. Roosting birds like the open spaces around the runways. Due to this fact, approximately ninety percent of the bird strike damages occur around airports. Statistics show that bird strikes are growing in number due to (1) the increase in bird population, (2) nesting of more birds in urban areas, (3) fewer natural predators of birds, and (4) the marginal effectiveness of common bird harassment techniques. Bird strikes therefore remain a very dangerous and costly problem.

A further example of the problems, which can arise at the interface between birds and humans, are the effects of the presence of birds in areas for public gatherings.

For example, the ubiquitous presence of bird feces in public places presents problems of sanitation for people. Furthermore, the deposition of bird feces on metal surfaces often causes problems of corrosion. Birds, such as woodpeckers, also frequently cause damage to woody and other non-metal surfaces by pecking on them. Birds are also frequent inhabitants of the exposed steel and concrete framework of structures, such as sports arenas and aircraft hangars, from which their feces present problems to both equipment and people. In addition, roof damage often occurs at locations where the flashing becomes corroded by bird feces.

Over the course of many years, a large number of procedures have been suggested and tried to overcome the above-described problems associated with birds and man-made structural surfaces. However, these have largely had only limited success. One example of such devices is an ultrasonic device which birds, but not humans, can hear. Another approach is to coat the problem surfaces with a sticky liquid or gelatin which birds find uncomfortable. Of course, the classic bird repellent method is the use of scarecrows or other arrangements which are frightening to the birds by virtue of their appearance and movement. A still further technique is the use of replicas of predators such as hawks, eagles and owls. Flashing lights have also been used for this purpose. Even the sound of cannons has been used. None of these, however, has been sufficiently effective because (1) the deterrent effect does not last long; (2) they are expensive to run; (3) they constitute a nuisance to humans in the vicinity; or (4) they require too frequent maintenance.

Therefore, a serious need continues for a reliable and economical method to deter birds from alighting on, occupying and damaging plant and structural surfaces in such manner that neither the environment nor the birds are harmed.

SUMMARY OF THE INVENTION

In its primary aspect, the invention is therefore directed to a method for deterring birds from roosting, loafing and perching on plant and solid or structural surfaces comprising applying to the surface a non-toxic composition that triggers a physiological aversion mechanism in said birds.

BRIEF DESCRIPTION OF THE DRAWING

The Drawing consists of three sheets. The first sheet contains FIGS. 1(a) through 1(e), in which various particulated forms of polycyclic quinone are depicted schematically. The second sheet contains FIG. 2, which is a graphical representation of the data obtained in Example 2. The third sheet contains FIGS. 3, 4, and 5, which are bar graphs representing the data obtained in Example 7.

DETAILED DESCRIPTION OF THE INVENTION

Introduction

Figure 2:
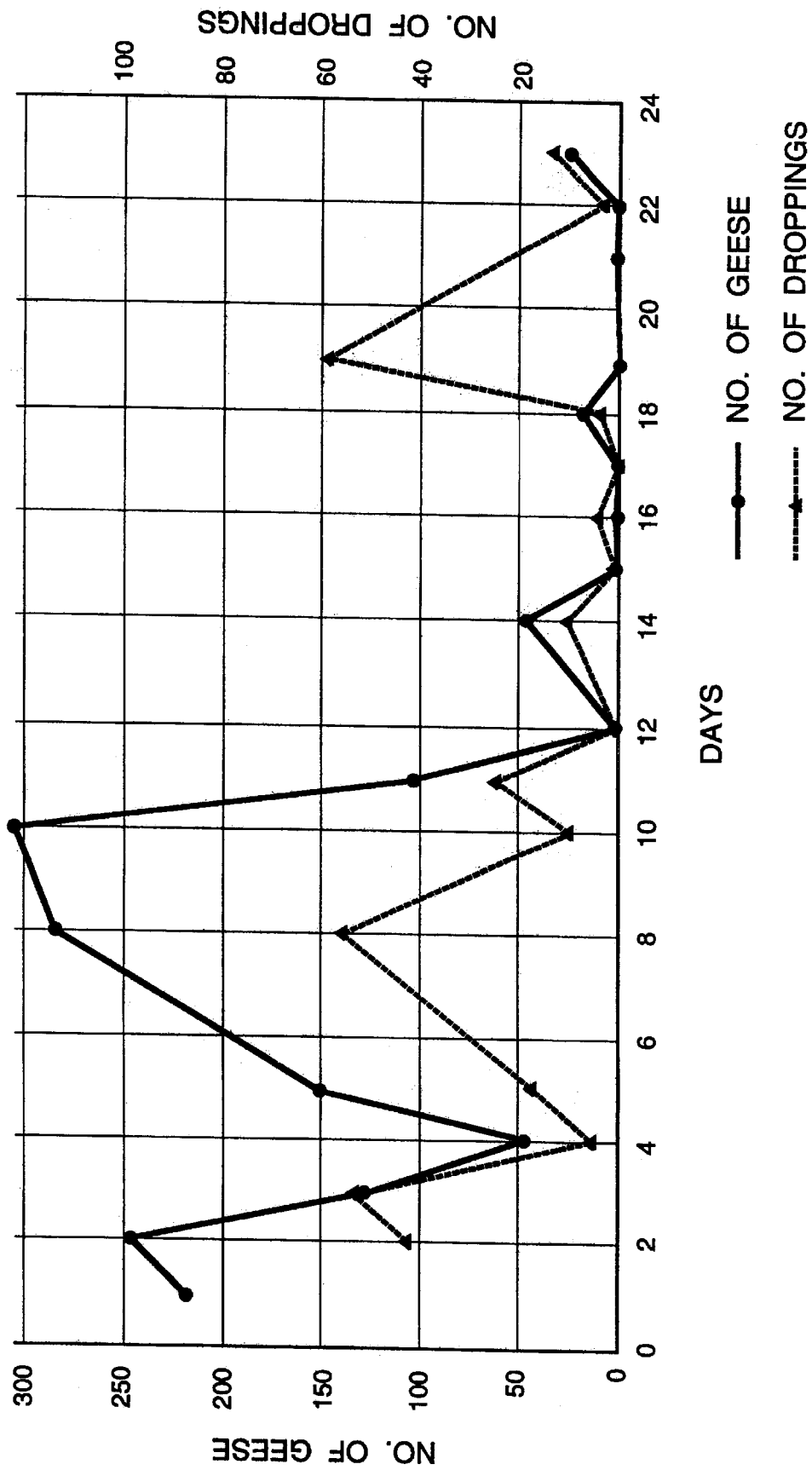

Many kinds of wildlife use visual cues to identify food in the environment in a manner similar to humans. Most species of animals use both long distance vision and close visual inspection to recognize food. In the case of birds, however, the visual acuity is much different than that of humans. Humans are capable of sensing light having a wave length in the single range of 400 to 700 nm. However, birds can see light in two visual spectra simultaneously. In particular, birds can detect light in the wave length ranges of 500–700 nm as well as 300–400 nm. Thus, birds can identify food which reflects light in the ultra violet range, which is invisible to humans, down to the limits of the sun "UV radiation at the earth" surface.

Using these principles, applicants have determined that a broad class of polycyclic quinones, which absorb light in various wave lengths within the range of 200–300 nm and which have taste or post-ingestional response, are effective to repel birds from feeding on a wide variety of plant seeds and surfaces It is not necessary that the light-absorbing materials absorb light throughout the range of 200–300 nm. It is sufficient that the material absorb a narrow band of light within that range sufficient to bring about a visually detectable shift in color perception by the bird. Thus, even if a narrow wave length-absorbing material is used, the surface is nevertheless distinctly marked by the resultant shift in the color of the coated surface as perceived by the bird.

In some cases, the bird is deterred by the color shift alone. In other cases, it appears that the bird samples the material. The total repellency effect of the compositions of the invention is, therefore, based on both sampling the compound and visual detection. In its broadest aspect, the invention is, therefore, directed to the use of non-toxic organic materials, which absorb light within the range of 200–400 nm, and which cause post-ingestional irritation or response when consumed.

Polycyclic Quinones
Composition

A wide variety of polycyclic quinones can be used in the invention. As used herein, the term "polycyclic quinone" refers to bicyclic, tricyclid and tetracyclic condensed ring quinones and hydroquinones, as well as precursors thereof. On the whole, the non-ionic polycyclic quinones and polycyclic hydroquinones (herein referred to collectively as PCQs) have very low solubility in water at ambient temperatures. For use in the invention, it is preferred that such PCQs have a water solubility no higher than about 1,000 ppm, by weight.

However, as noted above, certain precursors of such PCQs can also be used in the invention, either combined with the relatively insoluble PCQs or by themselves. Such precursors are anionic salts of PCQs which are water soluble under alkaline anaerobic conditions. However, these materials are not stable and are easily converted to the insoluble quinone form upon exposure to air. Thus, when anionic PCQs are applied to plants and exposed to air, they are quickly changed to the water-insoluble, more active quinone form.

Among the water-insoluble PCQs that can be used in the invention are anthraquinone, 1,2-dihydroxy anthraquinone, 1,4-dihydroxy anthraquinone, naphthoquinone, anthrone(9,10-dihydro-9-oxo-anthracene), 10-methylene-anthrone, phenanthrenequinone and the alkyl, alkoxy and amino derivatives of such quinones, 6,11-dioxo-1H-anthra[1,2-c]pyrazole, anthraquinone-1,2-naphthacridone, 7,12-dioxo-7,12-dihydroanthra[1,2-b]pyrazine, 1,2-benzanthraquinone, 2,7-dimethylanthraquinone, 2-methylanthraquinone, 3-methylanthraquinone, 1-aminoanthraquinone and 1-methoxyanthraquinone. In addition, more complex polycyclic quinone compounds can be used, such as 2-carboxy-1,3,5,6,8-pentahydroxy-7-monosaccharide and other saccharides of anthraquinones or glucosamides and 2(1,3-dihydro-3-oxy-5-sulfo-2H-indol-2-ylidine)-2,3-dihydro-3-oxo-1H-indole-5-sulfonic acid, disodium salt. Of the foregoing cyclic ketones, anthraquinone and 1,4-dihydroxyanthraquinone are preferred because they appear to be more effective. Naturally occurring anthraquinones can be used as well as synthetic anthraquinones.

Other PCQs which can be used include insoluble anthraquinone compounds, such as 1,8-dihydroxy-anthraquinone, 1-amino-anthraquinone, 1-chloro-anthraquinone, 2-chloro-anthraquinone, 2-chloro-3-carboxyl-anthraquinone and 1-hydroxy-anthraquinone. Various ionic derivatives of these materials can be prepared by catalytic reduction in aqueous alkali.

In addition, a wide variety of anthrahydroquinone compounds can be used in the method of the invention. As used herein, the term "anthrahydroquinone compound" refers to compounds comprising the basic tricyclic structure such as 9,10-dihydroanthrahydroquinone, 1,4-dihydroanthrahydroquinone, and 1,4,4a,9a-tetrahydroanthrahydroquinone. Anthrahydroquinone itself is 9,10-dihydroxyanthracene.

More particularly, both water-insoluble and water-soluble forms can be used. The non-ionic compounds are largely insoluble in aqueous systems, while ionic derivatives, such as di-alkali metal salts, are largely soluble in water. The water soluble forms are stable only in high pH anaerobic fluids. Low pH fluids (pH less than about 9–10) will result in the formation of the insoluble molecular anthrahydroquinone. Aerobic solutions will incur oxidation of the anthrahydroquinones to anthraquinone. Thus, anthrahydroquinones will not exist for long periods of time in an aerated environment, such as that which is experienced by spraying. For these reasons, anthrahydroquinone treatments are usually implemented with the soluble ionic form in a caustic solution. Sodium hydroxide solutions are preferred over the hydroxides of other alkali metals for economic reasons.

Configuration

The PCQ used should be in physical form small enough to be touched by the sensory organs of the bird. Thus, for the PCQ to be more effective as a repellent, it is preferred to be of sufficiently small particle size that its presence can be sensed. Thus, the more effective quantity of repellent in any application is that which is in a form accessible to the birds' nerve endings; that is, it should be of sufficiently small size that it can be orally sensed.

Generally, because of these criteria, particles larger than about 50 micrometers cannot be adequately sensed and particles no larger than 30 micrometers are preferred. Similarly, smooth continuous surfaces of PCQ cannot be adequately sensed; and, of course, if the PCQ is coated with anything which is non-repellent to the bird or to which the bird is taste insensitive, the PCQ is ineffective. Though, strictly speaking, for the PCQ to be effective as a repellent it does not have to be in the form of discrete particles; nevertheless, the particles must be of sufficient size or have a contour that contains areas that are taste-accessible. This criterion is illustrated in the Drawing.

The particle in FIG. 1(a) would be accessible because it is sufficiently small. The particle in FIG. 1(b) would be less effective because it is too large to be sensed effectively. The smooth continuous coating in FIG. 1(c) would create little or no taste sensation because the large continuous surface would not have adequate access to the birds' nerve endings. On the other hand, the continuous coating shown in FIG. 1(d) would create at least moderate taste sensation because the protrusions on the coating are sufficiently small to be tasted. In this situation, the PCQ in the protrusions would be effective, but the PCQ in the main body of the coating would be less so, if at all. When the particles are portrayed as stacks of particles, as in FIG. 1(e), it can be seen that some of the particles in the upper layers would be accessible and therefore would be effective; but those particles in the lower layer would be less accessible and therefore less effective. The foregoing analysis shows clearly that the efficacy of the repellent is a function of both its configuration and accessibility. In turn, it can be seen that these variables are in large part dependent on the method of application.

When the PCQ is applied directly in particulate form, the size of the particles can be readily controlled. When such particles are applied as a single layer of particles, substantially all of the PCQ would be effective. However, if the particles are applied as a multiple of particle layers, essentially only the top layer would be effective. An important aspect of this analysis is that it is not important that the PCQ be applied as continuous covering. To the contrary, it is better that the coating of PCQ particles be discontinuous, at least on a micro scale, to enable functional exposure of the stomata of the foliage. Thus, the particles to be effective must be "particulated" in the sense that they contain areas which are accessible to the avian taste nerve endings.

It is the inventor's determination, in view of the Examples, that it is preferred that the polycyclic quinone be applied to the surface to be treated at a level ranging from 0.2 mg/sq meter to 50 mg/sq meter of surface. It is more preferred that the polycyclic quinone be applied to 25 mg/sq meter of surface to be treated.

Physical Properties—Volatility, Water Solubility

It is important to the effectiveness of the invention that the PCQ, in whatever physical form it is applied, be persistent. That is, the applied active material must be able to resist erosion by wind and rain and other environmental forces to which the treated surface is exposed. For this reason, it is preferred (1) that the active form of the PCQ have a relatively low solubility in water so that it is not easily washed off the treated surfaces, and (2) that it have a relatively high melting temperature so that it does not undergo excessive evaporation or sublimation from the treated surfaces during exposure to high ambient temperatures. For these reasons, it is preferred that the active PCQ material has a solubility in water under ambient temperature conditions of no more than about 1000 ppm and preferably at least 10–200 ppm and that the melting temperature of the active PCQ component be at least about 150 C. and preferably at least 200 C.

Even when the active PCQ material possesses the above-described preferred physical properties, the material may have poor persistence because it does not adhere well to the surface to which it is applied. This is a function of the different properties of the surface and the PCQ material. When this occurs, it is further preferred that the formulation contain a "sticking agent", i.e., a material which itself has good adhesion to the substrate and when mixed with the active material causes the PCQ to adhere to the substrate more firmly. Preferred sticking agents are aqueous polymer lattices, which upon evaporation of the water therefrom, form a polymeric mass which is highly adhesive to the plant surface and holds particles of the active material firmly on the plant or solid surface. Such sticking agents typically contain a small amount of surfactant dissolved in the aqueous phase.

Even though highly water-insoluble PCQ compounds are preferred, less insoluble compounds are nevertheless usable in the invention under conditions in which they are not unduly exposed to conditions by which they are washed off. Furthermore, the use of water-resistant sticking agents can be used to mitigate the washing effect of heavy rains.

A distinct advantage of the PCQ compounds that have been tested for use in the invention is that they are essentially non toxic, i.e., they have an $LD_{50}$ of at least 2,000 mg/kg in rats and preferably an $LD_{50}$ in rats of 5,000 mg/kg or higher. Because of this low toxicity of PCQs, they are not toxic to most insects or to birds, animals and humans. Moreover, the toxicity level is sufficiently low that any active material that becomes leached into the soil will not be detrimental to the normal constituents of fertile soil layers.

It is important to note that the source of the PCQ used for bird repellency is an important criteria to ensure low toxicity. For example, applicants have registered with the U.S. EPA the PCQ known as 9,10-anthraquinone as a safe, non-toxic PCQ for use as a bird repellent (see U.S. EPA Pesticide Fact Sheet for Anthraquinone, December 1998). It is within the scope of those having ordinary skill in the art to substitute other non-toxic PCQ's in place of anthraquinone for use in the present invention.

Coadjuvants

As used herein, the term "coadjuvant" refers to materials which have a bio-activity different than the polycyclic quinones themselves. Such materials include contact repellents, fungicides, pesticides, and mixtures thereof. Both liquid and solid coadjuvants can be used in conjunction with the PCQ's of the invention, depending on the manner of application. (See discussion below.) It should be noted, however, that the use of fungicides and pesticides as adjuvants may not be preferred because of the poisonous nature of such adjuvants.

An important class of coadjuvant for use in combination with the PCQs are trigeminal repellents, i.e., repellents which repel birds when the bird tastes the material. It has been found that terpene-based compounds are particularly useful for this purpose. Limonene, pinene and pulegone are terpenes which are preferred for this purpose. However, polymeric terpenes are also useful for this purpose, especially low molecular weight polymeric terpenes, which are sticky in character.

When terpenes are used as co-repellents with PCQs, they will ordinarily constitute a major part of the composition and the PCQs will constitute only a minor part. For example, composition comprising as little as 1% wt. PCQ in terpene (including polymeric terpenes) can be used effectively. Though still higher PCQ concentrations can be used, it will not be necessary to use more than about 10% wt. On the other hand, as little as 10% wt. terpene compound can be used, at least 30% being preferred to enhance the contact repellency properties.

Other trigeminal repellents, such as pepper and 2-hydroxyacetophenone, and methylanthranalate, can also be used in admixture with the PCQ and admixtures of PCQ with other trigeminal repellents.

Additives

As used herein, the term "additives" refers to materials which augment the effectiveness of the compositions of the invention, but which do not by themselves have bio-activity. These include such materials as surfactants, wetting agents, defoaming agents, extenders, sticking agents, penetrants, plasticizers, activators, spreading agents, diluents, odorants and the like.

When the PCQs are in powder form, they can be dispersed in a liquid media, especially water, and sprayed as a liquid suspension. On the other hand, when water-soluble precursors of the PCQs are used, they can be dissolved in water for dilution and then applied by spraying in the usual manner. The aeration, which occurs during spraying is sufficient to convert the soluble salt to the more active water-insoluble form. In both of these techniques either solid or liquid coadjuvants can be used. For example, water-soluble coadjuvants can be dissolved in the liquid medium or water-insoluble coadjuvant particles can be suspended in the liquid medium along with the PCQ and/or PCQ precursor.

In general, quite dilute applications of the PCQs to surfaces are effective to deter bird presence. For example, the application of liquid dispersions containing as little as 100 ppm by weight PCQs can be effective. At least 1000 ppm is preferred. It will be recognized, however, that the effective dose level of the active component varies widely, both with the type of bird infestation and the composition of the active component. Fortunately, higher concentrations of PCQs can be tolerated with complete safety both to the environment, to humans, and to the birds to be deterred.

It will be recognized from the foregoing discussion that not all of the PCQ coatings may be of suitable configuration. However, so long as a sufficient fraction of the coating is available to the birds' nerve endings, the composition will effectively deter them from the surface. As mentioned above, access of the PCQ repellent to the oral sensors of the bird may occur during preening of body parts which contain the repellent as a result of contact with the treated surfaces.

It will be recognized that other dispersion media than water can be used. For example, safe, degradable oils, such as vegetable oils, can be used. However, from the standpoint of safety and environmental health, it is much preferred to use water.

EXAMPLES

In the following Examples, three series of tests were carried out to observe the efficacy of the invention to deter birds from perching, loafing and/or roosting on areas of grassy turf, and structural surfaces.

Deterrence from Loafing/Roosting on Areas of Grassy Turf

Example 1

A formulation containing 50% wt., basis total formulation, of 9,10-anthraquinone dispersed in water with a small amount of surfactant and thickener was prepared and sprayed onto untreated grassy turf in an area where geese normally loaf or roost. One-third acre of turf was treated with areas of untreated turf bordering on both sides of the treated area. The dispersed anthraquinone particles were applied at a rate of 1 pint/acre (approximately 50 mg/m$^2$) on the treated area. The test areas were observed for approximately four weeks to determine the effects of the treated versus the untreated areas. The differences in the effects of the treated area versus the untreated area were easily noted. Geese loafing/roosting in the untreated areas were unaffected and exhibited normal behavior as they fed and were not repelled. Geese that entered the treated area began to feed, but immediately ceased eating, exited the treated area, entered a nearby pond and began to wash or rinse themselves. After this exhibited behavior, none of the geese feeding on the untreated areas entered the treated areas. The geese were repelled from the treated area for approximately two weeks until the turf was cut. After cutting, another treatment was applied. The dispersed anthraquinone particles were applied at a rate of ½ pint/acre (approximately 25 mg/m$^2$) in the same manner of treating one strip of turf bordered by untreated turf. The same repellency was exhibited. The test was continued for approximately two weeks. The test was concluded due to snow.

Example 2

A grassy test site having an area of 6.2 acres was selected within the grounds of a large campus style research complex having a substantial flock of geese in residence, which numbers 250–300 geese during the day and as many as 500 geese in the evening hours. In order to determine when daily observations should be made, the site was observed beforehand to determine the times during which the maximum number of geese were on the test site. Observations were conducted at the same time(s) each day in such manner that the behavior of the geese could be observed without disturbance. In addition, the number of droppings in selected areas of the site were counted each day, recorded and then removed from the test area by raking.

Following 10 days observation of the untreated test site, the above-described goose repellent composition was sprayed on the test area using a calibrated spray tank and a fan-shaped head sprayer. The liquid spray contained one gallon of repellent per 140 gallons of water and the rate of application was 2.77 pounds of AQ per acre of the mixture. In the absence of rain, the applied composition fully dried on the blades of grass within 24 hours.

Figure 3:
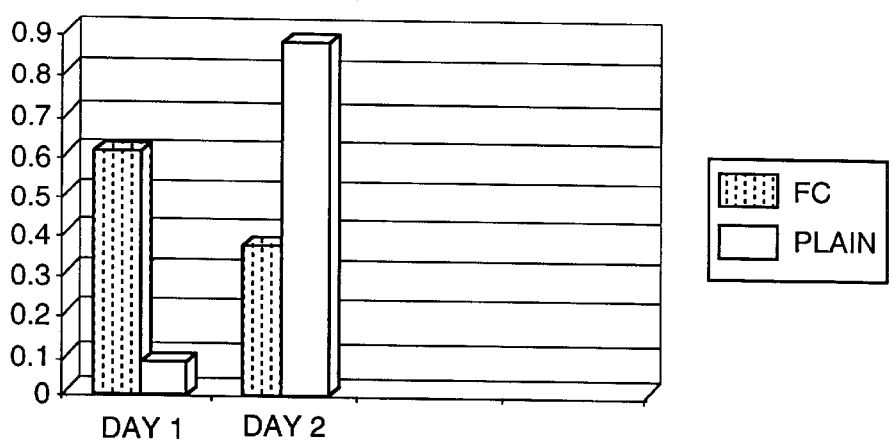

During the week before application of the repellent composition, the goose counts taken in the afternoon were from about 45 to 305 geese with an average of about 150 geese. Following application of the bird repellent composition, the goose count was about 110 the following day, but dropped to zero a day later. More complete test data are given in FIG. 3 of the Drawing.

Turning now to FIG. 2 of the Drawing, it can be seen that between days 1 and 3, the number of geese in the test area dropped substantially from over 200 to 48. This drop in the number of geese appears to have resulted from the departure of a migrant flock from the test area. However, the number of geese began to grow in day 5 and reached a maximum of over 300 by day 10 of the test. After making the count on day 10, the test area was treated with PCQ's in the manner described above.

By day 11, the number of geese dropped to 109 and on day 12 the number of geese was reduced to zero. During days 12–23, only a few geese were observed from time-to-time. On day 18, several geese (18) were observed in the test area; but, as indicated by the very low quantity of droppings, it is apparent that the flock, which was probably migratory, was repelled from the test area before the next day. Following a heavy rain, on day 23, the goose count rose to 27 and the number of droppings rose to 13. This minor increase in the number of geese appeared to result from some of the treating material's being washed off the grass. After treatment of the test area, large numbers of birds were observed milling around, but not entering the treated area.

Since completion of the tests carried out in this Example, it has been noted that the number of geese in the treated area, as compared to the number in the surrounding untreated areas, remained quite low for a period more than 3 months following the treatment. This phenomenon was quite unexpected in view of the fact that the treating material in the test area had been largely dissipated by heavy rains. Such prolonged deterrent effect is believed to be a result of memory by the geese who had initially been exposed to the polycyclic quinone treating material.

Deterrence from Roosting/Loafing on and Occupying Structural Surfaces

In the following examples, the treating material was an aqueous dispersion of small particles of 9,10-anthraquinone containing 50% by weight of the anthraquinone and a small amount of surfactant.

Example 3

A large number of seagulls regularly roosted on the flat roof of an industrial building in Northern California. Upon application to the roof of the above-described composition, the gulls did not further use the surface for roosting.

Example 4

In Philadelphia Pa., a large number of crows, estimated at over two hundred thousand, regularly roosted on the flat roof of an industrial building. Upon spraying the surface of the roof with the above-described composition, the crows did not return.

Example 5

Pigeons regularly roosted on the exposed steel beams within a large aircraft hangar in Wilmington Del. Upon spraying exposed surfaces of the exposed steel beams with the above-described composition, the pigeons did not return.

Example 6

Four ounces of a 50% by weight dispersion of anthraquinone in water were mixed with 29 gallons of water. The mixture was sprayed on a twenty foot section of a metal beam in the superstructure of a large sports arena. The treated beam section was open to the atmosphere and had become a roost for pigeons. Prior to the treatment, a section of walkway beneath the beam was cleaned weekly of 50–60 bird droppings. After more than 30 days following treatment of the beam with the above-described dilute anthraquinone dispersion, the pigeons had not returned to the roosting site.

Example 7

Evaluation of AQ as an Avian Perching Deterrent
Methods

Two (2) pens (10×20×6 feet) constructed of wood and aviary wire in a roofed outdoor aviary with a concrete floor were erected. At one end of each pen a water bowl and a food bowl containing the birds' maintenance diet was provided. On the morning of day 1, the test birds were transferred from their holding cages to each of the test pens. In each pen, there was one centrally located perch. At 0800 on the morning of day 2, this perch was removed and 2 test perches were installed, one in each of the corners at the end of the pen away from the food and water. For red-winged blackbirds (*Agelaius phoeniceus*) and brown-headed cowbirds (*Molothrus ater*), the perches were made of aluminum rod, 1.2 m long and 1.0 cm in diameter. For fish crows (*Corvus ossigragus*), the test perches were hollow stainless steel pipe, 1.2-m long and 2.25 cm in diameter. One of the test perches (randomly determined) was coated with a product containing 50% AQ as the active ingredient (the "repellent"), and the other was uncoated. The repellent was applied to the perches with a paint brush 24–48 hours before the test. The repellent was easily applied and appeared somewhat like thinned paint. It covered the metal surfaces very well, with some streaking, and formed an opaque coating that was dry to the touch by the start of the trial. Approximately 7.5 g wet weight was applied to each crow perch and approximately 3.5 g to each blackbird/cowbird perch.

Test perches remained in the pens until 1500 on day 3 at which time the birds were captured, banded and released. The activity was videotaped in each pen during 3 30-min periods daily: 0800–0830, 1100–1130, and 1400–1430. The videotapes were reviewed to determine bird use of the perches. The number of birds on each of the test perches were recorded at 1-min intervals. Activity and locations of birds not on the perches was also noted. Five (5) groups of blackbirds and cowbirds and 4 groups of fish crows were tested. For blackbirds and cowbirds, there were 4 birds in each test group. For fish crows, we used 2 birds per pen.

To analyze responses of the birds to the perch treatment, the mean number of birds on each perch during each of the 6 30-min observation periods was used. The data are expressed as birds/min. A separate 2-way repeated measures analysis of variance for each of the 3 bird species was performed to test the null hypothesis of equal use between the two perches.

Results

Red-winged blackbirds—Use of the untreated perch (x=0.86 birds/min., SE=0.10) was more than twice (P=0.067, $F_{1,8}$=4.50) that of the treated perch (x=0.41 birds/min, SE=0.06). Total perch use did not vary between days (P=0.557, $F_{1,48}$=0.35). There was a strong interaction between day and perch (P<0.001, $F_{1,48}$=11.49) that reflected increased use of the untreated perch and decrease use of the treated perch from day 1 to day 2 (Table 1)

Brown-headed cowbirds—Use of the untreated perch (x=1.70 birds/min, SE=0.23) exceeded (P=0.015, $F_{1,8}$=9.47) that of the treated perch (x=0.62 birds/min, SE=0.14). Total perch use declined (P=0.003, $F_{1,48}$=9.47) from day 1 (x=1.51 birds/min., SE=0.22) to day 2 (x=0.81 birds/min., SE=0.17). There was no interaction between day and perch (P=0.222, $F_{1,48}$=1.53) as bird use of each perch declined on the second day (Table 2).

Fish crows—Use of the untreated perch (x=1.28 birds/min., SE=0.08) was approximately twice (P=0.014, $F_{1,6}$=11.70) that of the treated perch (x=0.64 birds/min., SE=0.08). Total perch use did not vary between days (P=0.734, $F_{1,38}$=0.12). The interaction between day and perch (P=0.090, $F_{1,38}$=3.03) reflected increased use of the untreated perch and decreased use of the treated perch from day 1 to day 2 (Table 3).

Discussion

Over the course of these 2-day trials, each of the 3 test species displayed a preference for the untreated perch over the one coated with repellent. Heretofore, the repellent has been considered a feeding deterrent, with the active ingredient, 9,10-anthraquinone, causing postingestional distress or imitation to birds eating treated food. It is somewhat surprising therefore to find that birds also find it unappealing to use perches painted with this repellent.

The mechanism of this apparent perch repellency is unclear. No initial reluctance by birds to use the treated perches was observed, so it is unlikely that the appearance of the treated perch was offensive. Similarly, when birds perched on the treated perch, no indication that they were uncomfortable or bothered by the feel of the perch was observed, so an adverse tactile stimulus can be ruled out. Contact irritation would not be expected as birds, exposed to anthraquinone on food display no sign of irritation.

Dermal uptake through the feet, however, is a possible route of exposure. The extent to which this might have occurred is unknown, but dermal toxicity of Flight Control is low (acute dermal $LD_{50}$ in rats>5000 mg/kg, pesticide fact sheet for anthraquinone, U.S. Environmental Protection Agency, December 1998).

Accidental ingestion of the repellent is another possible means by which birds might have been exposed. Birds frequently wiped their bills on the perch when they returned from feeding or drinking. Birds also used their feet to scratch the facial area around the bill. It is possible that during these maintenance activities, the birds accidentally ingested the repellent. Conceivably, through repeated exposure in this manner, birds could have associated illness or malaise with the treated perch and acquired a learned avoidance response. On the videotapes, no sign of illness was observed (e.g. decreased activity, fluffed fethers, vomiting).

Figure 4:
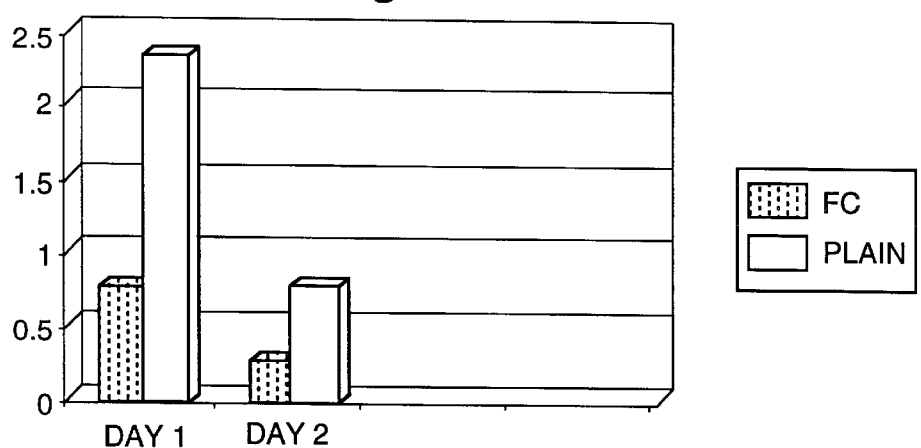
Figure 5:
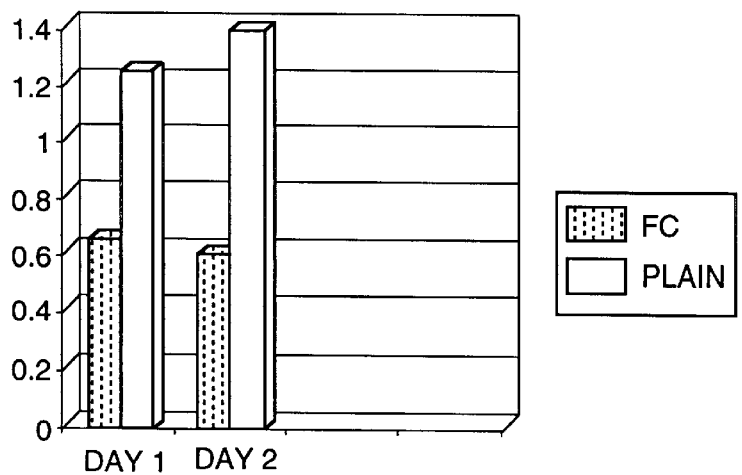

The temporal patterns of perch use exhibited by red-winged blackbirds (FIG. 3) and fish crows (FIG. 5) are consistent with learned avoidance. For each species, differential use of the untreated perch increased from the first to the second test day. Conversely, cowbird behavior was not consistent with this pattern (FIG. 4). Cowbirds tended to reduce their use of both perches which suggests that they were not able to distinguish the source of their discomfort. Thus, they spent more time on the floor of the pen.

Pen and field observations of bird behavior were made throughout the studies. In no situation were adverse effects or discomfort to the observed birds. In feeding on rice seeds, the birds squeezed the grain from the hull then ejected the hull from their mouths and ate only the inner grain. During this feeding activity, which maximized contact with AQ, the treated seeds did not affect the birds' behavior or induce pain. Consumption of AQ did not affect feeding behavior, in terms of grams of feed per day.

Upon completion of all studies, the test birds were released near the original point of capture. No test birds died due to exposure to the AQ. In a separate study, we found the $LD_{50}$ of AQ in northern bobwhite quail to be in excess of 2,000 mg/kg body weight.

What is claimed is:

1. A method for deterring birds from roosting, perching or loafing on a plant or solid surface comprising applying to the surface a non-toxic deterrent consisting of 9,10-anthraquinone that triggers one or more of the following, a visual cue or a post-ingestional response, in said birds, wherein the 9,10-anthraquinone is in the form of finely-divided particles having an average size of less than 50 micrometers and wherein the 9,10-anthraquinone is applied at a level of at least 0.2 mg/sq meter.

2. The method of claim 1 wherein the 9,10-anthraquinone comprises an aqueous dispersion selected from non-toxic finely divided particles of (1) polycyclic quinone and (2) hydroquinone in suspension and alkali salts of anthrahydroquinones in solution.

3. The method of claim 1 wherein the 9,10-anthraquinone absorbs light having a wavelength in the range of 250 nm.

4. The method of claim 1 wherein the 9,10-anthraquinone is applied at a level of 25 mg/sq meter of treated surface.

5. The method of claim 1 wherein the 9,10-anthraquinone contains at least one additive selected from the group consisting of sticking agents, surfactants, taste repellents, terpene-based compounds.

6. The method of claim 1 wherein the 9,10-anthraquinone has a solubility in water of no more than 1,000 ppm by weight at its highest temperature of exposure.

7. The method of claim 1 wherein the 9,10-anthraquinone has a melting point of at least 50 C.

* * * * *